United States Patent [19]

Kristensson et al.

[11] Patent Number: 4,592,869
[45] Date of Patent: Jun. 3, 1986

[54] SELECTIVE ACYLATION PROCESS

[75] Inventors: Sten K. Kristensson; Anders R. Stamvik, both of Helsingborg, Sweden

[73] Assignee: Aktiebolaget Leo, Helsingborg, Sweden

[21] Appl. No.: 655,950

[22] Filed: Sep. 28, 1984

[30] Foreign Application Priority Data

Oct. 12, 1983 [SE] Sweden ............................ 8305596

[51] Int. Cl.⁴ ................................................ C07J 1/00
[52] U.S. Cl. .............................. 260/397.4; 260/397.5; 546/1
[58] Field of Search ............... 260/397.5, 397.3, 397.4; 546/1

[56] References Cited

U.S. PATENT DOCUMENTS 4,180,504 12/1979 Hansen et al. ............ 260/239.55 D

OTHER PUBLICATIONS

Steroids, (1984), vol. 44, No. 1, pp. 85–93.
Delaney, E. J. et al., in J. Am. Chem. Soc. 104, (1982), 799–807.
Tomoi, M. et al., in Makromol. Chem. Rapid Commun. 3, (1982), 537–542.

*Primary Examiner*—Elbert L. Roberts
*Attorney, Agent, or Firm*—Gordon W. Hueschen

[57] ABSTRACT

This invention relates to a selective acylation process for the preparation of phenolic N-disubstituted carbamate esters of steroids, comprising reacting in an inert solvent an acylating agent being a carbamoyl halogenide, a 4-(tertiary amino)-pyridine, or a complex thereof, optionally as a part of a polymer and a steroid having at least two free hydroxy groups, where at least one is phenolic and at least one is alcoholic, optionally in the presence of an acid acceptor.

23 Claims, No Drawings

SELECTIVE ACYLATION PROCESS

FIELD OF INVENTION

This invention relates to a novel method for selective acylation of phenolic hydroxy groups in steroids using a 4-(tertiary amino)-pyridine or reactive complexes thereof.

BACKGROUND OF INVENTION

Prior art 4-(tertiary amino)-pyridines are disclosed in e.g. Angew. Chem. Int. Ed. Engl. 17, 569–583 (1978). In this publication the extremely strong catalytic effect of these pyridines is discussed. The high catalytic activity can be used for acylating even sterically hindered secondary or tertiary alcohols, and sterically hindered alcoholic OH-groups in steroids where other methods fail. As regards the effect of this catalyst in acylating phenolic hydroxy groups it is stated that the catalysts effect a similar increase in reaction rate as is found in the case of alcohols, and specific examples are disclosed for the acylation agents acetic anhydride and dimethyl carbamoyl chloride.

SUMMARY OF THE INVENTION

The selective acylation according to the present invention comprises reacting in an inert solvent an acylating agent being a carbamoyl halogenide, a 4-(tertiary amino)-pyridine, or a complex thereof and optionally as a part of a polymer, and a steroid having at least two free hydroxy groups, where at least one is phenolic and at least one is alcoholic, optionally in the presence of an acid acceptor, for the preparation of N-disubstituted carbamate esters of steroids. The remaining alcoholic hydroxy group(s) may be optionally converted to other ester groups by conventional methods.

In view of what is known from prior art it was quite surprising that the acylating agent, which according to the invention constitutes a carbamoyl halogenide, gives a selective acylation of the phenolic hydroxy group(s) in a steroid also substituted by one or more alcoholic hydroxy groups.

Accordingly one object of the invention is to provide a selective acylation method for the preparation of phenolic carbamate esters of steroids.

Another object is to provide such a method characterized by high yields.

A third object is to provide a method for the preparation of phenolic carbamate esters which could be used for various purposes, e.g. as pharmaceuticals, e.g. antitumour agents, such as estradiol-3-N-bis-(2-chloroethyl)carbamate, and as intermediates for preparing such useful compounds, e.g. estradiol-3-N-bis(2-chloroethyl)carbamate-17-phosphate or salts thereof (see e.g. U.S. Pat. No. 3 299 104).

A fourth object is to provide new complexes between certain carbamoyl halogenides and 4-(tertiary amino)-pyridines, which e.g. can be used in the present invention.

The group of steroids suitable to be used according to the invention comprises substituted estra-1,3,5(10)-trienes.

It is preferred that these estra-1,3,5(10)-trienes are substituted by only one phenolic hydroxy group, which is situated in the 3-position and that the alcoholic hydroxy group(s) is(are) situated in 16- and/or 17-position whereby, if present in both, one of them may be in the form of an ester.

As examples of such steroids the following estrogens may be mentioned: estra-1,3,5(10)-triene-3,17$\beta$-diol(estradiol-17$\beta$), estra-1,3,5(10)-triene-3,17$\alpha$-diol(estradiol-17$\alpha$), estra-1,3,5(10)-triene-3,16$\alpha$, 17$\beta$-triol(estriol), estra-1,3,5(10)-triene-3,16$\beta$,17$\beta$-triol (16-epi-estriol), estra-1,3,5(10)-triene-3,16$\alpha$,17$\alpha$-triol(17-epiestriol), estra-1,3,5(10)-triene-3,16$\alpha$-diol-17-one, estra-1,3,5(10)-triene-3,17$\beta$-diol-16-one, (16-ketoestradiol), 17$\alpha$-ethynyl-estra-1,3,5(10)-triene-3,17$\beta$-diol(17$\alpha$-ethynylestradiol) and estriol-16-acetate.

Among the estrogens mentioned above the following are particularly preferred: estradiol-17$\beta$, estriol, estriol-16-acetate, and 17$\beta$-ethynyl-estradiol, especially estradiol-17$\beta$.

Suitable acylating agents are N-disubstituted carbamoyl halogenides, especially substituted N-dialkyl carbamoyl chlorides, where it is preferred that said alkyl groups are the same or different and are selected from ethyl or propyl and preferably substituted with a halogen atom, such as Cl or Br in 2- or 3-position. N-bis(2-chloroethyl)carbamoyl chloride is especially preferred.

Unsubstituted N-dialkyl carbamoyl halogenides such as N-diethyl carbamoyl chloride can also be used but result in a considerable decrease in yields (see Example 3).

The 4-(tertiary amino)-pyridine used as a catalyst is a pyridine ring, optionally substituted with one or more methyl and/or ethyl groups situated in the 2-, 3-, 5- and 6-positions, and having a tertiary amino group, e.g selected from the group consisting of dimethylamine, diethylamino, pyrrolidinyl, piperidinyl, morpholinyl, 4-methylpiperidinyl and hexahydroazepinyl. Other suitable tertiary amino groups are found in the literature, e.g. in Hassner, A. et al, Tetrahydron 34 (1978) 2069. The groups described therein are incorporated herein by reference.

4-dimethylaminopyridine and 4-pyrrolidinyl-pyridine are preferred. Optionally the substituted pyridines can be used in the form of their acid addition salts, which under such circumstances are transformed to their free bases in the reaction mixtures by conventional methods.

The substituted pyridines are preferably used in a catalytic amount, e.g. in the range of 0.02 to 0.2 mole per mole of the steroid employed, and in the presence of an acid acceptor, but they can also be used in the form of their complex with the N-disubstituted carbamoyl halogenide either as directly formed in solution or in isolated form.

The complexes between N-disubstituted carbamoyl halogenides and 4-(tertiary amino)-pyridines are new and are 1-(N-disubstituted aminocarbonyl)-4-(tertiary amino)-pyridinium halogenides.

Preferred complexes are 1-(N-dihaloalkylaminocarbonyl)-4-(tertiary amino)-pyridinum chlorides where the halogen atoms are selected from Cl or Br situated in 2- and/or 3-positions. Most preferred complexes are 1-(N-bis(2-chloroethyl)-4-(tertiary amino)-pyridinium halogenides.

Especially preferred are 1-(N-bis(2-chloroethyl)aminocarbonyl)-4-dimethylamino-pyridinium chloride and 1-(N-bis(2-chloroethyl)aminocarbonyl)-4-pyrrolidinylpyridinium chloride.

According to the invention it is also possible to use the 4-(tertiary amino)-pyridines or the complexes described above attached to polymers, e.g. according to Delaney, E. J. et al in J. Am. Chem. Soc. 104 (1982) 799, or transformed to be part of polymers by polymerization processes such as described by Tomoi, M. et al, in Makromol. Chem. Rapid Commun. 3 (1982) 537. Those described therein are incorporated herein by reference. Such polymer-supported substituted pyridines are preferably used in a catalytic amount, calculated on their content of the substituted pyridines. They may also be used in the form of their complexes with carbamoyl halogenides.

The acid acceptors employed may be any conventional ones, as apparent to one skilled in the art. Tertiary amines are preferred and especially tertiary amines approximately equal to or stronger as bases than the 4-(tertiary amino)-pyridines used, e.g. acid acceptors such as triethylamine, diisopropyl-ethylamine and 1,8-bis(dimethylamine)naphtalene. The 4-(tertiary amino)-pyridines themselves may also be used as acid acceptors. The acid acceptors present, when the 4-(tertiary amino)pyridines are used in catalytic amounts, are employed in at least an amount necessary to bind the free hydrogen halide formed during the reaction.

The solvent employed may be any conventional solvent, well known in the art for acylation reactions, or a mixture of such solvents compatible with the reaction. Such solvent may be hydrocarbons, halogenated hydrocarbons, ethers, esters, ketones, or amides.

Among the halogenated and non-halogenated hydrocarbons the following may be mentioned as representative solvents: chloroform, methylene chloride, benzene, chlorobenzene, and toluene.

It is preferred that the ethers, esters, ketones, and amides are aliphatic. Representative examples of such solvents are dioxane, tetrahydrofurane, diethyl ether, ethyl acetate, acetone, butanone, and dimethyl formamide.

Chloroform, methylene chloride, chlorobenzene and toluene are the particularly preferred solvents.

Reaction temperature

The temperature is not critical except that it should not be so high as to produce undesirable side-effects, or so low that the reaction proceeds so slowly as to be at an uneconomic rate. The preferred range is from room temperature to the boiling point of the solvent employed.

Reaction pressure

The pressure used above the reaction mixture during the reaction is not particularly critical. For most purposes atmospheric pressure is adequate. In some cases, however, superatmospheric pressure may be desired and is suitable. The pressure may also be below atmospheric pressure if desired.

Reaction time

The reaction period may vary widely but for best yields and greatest economy the reaction must be allowed sufficient time to go to completion.

Molar ratios

The phenolic steroid and the carbamoyl halogenide or the 1-(N-disubstituted aminocarbonyl)-4-(tertiary amino)-pyridinium halogenides are generally employed in approximately molar amounts. However, a small excess of the carbamoyl halogenide or the 1-(N-disubstituted aminocarbonyl)-4-(tertiary amino)-pyridinium halogenides is normally favourable and does not give rise to any detrimental effect upon the reaction.

Work-up procedure

The reaction mixture containing the desired product is worked up according to normal procedures, as apparent to those skilled in the art.

The nomenclature used in this disclosure is in accordance with the rules issued by the IUPAC Commission on the Nomenclature of Organic Chemistry, 1957, 1965, and 1971.

The following examples are intended to illustrate but not to limit the scope of the invention, although the reagents named and the carbamates obtained are of particular interest for our intended purposes.

The NMR data given in the examples below are obtained from solutions in deuterated chloroform, using a 60 MHz instrument (Perkin Elmer R12). The following abbreviations have been used regarding the multiplicity of peaks: s=singlet, d=doublet, t=triplet, m=multiplet.

EXAMPLE 1

To a stirred suspension of 15 g of estradiol-17$\beta$ (55 mmol), 6.27 g of triethylamine (62 mmol) and 1.25 g of 4-N,N-dimethylaminopyridine (10 mmol) in 150 ml of chloroform is added a solution of 13.2 g N-bis(2-chloroethyl)carbamoyl chloride (65 mmol) in 50 ml of chloroform.

The mixture is vigorously stirred for 3 hrs at room temperature. A clear solution is obtained. The solution is washed with 50 ml of 0.5-M hydrochloric acid and then twice with 100 ml portions of water. The organic phase is dried over sodium sulphate, filtered and evaporated to dryness.

The residual oil which is the estradiol-17$\beta$, 3-N-bis(2-chloroethyl)-carbamate is recrystallized from 200 ml of methanol. The crystallized product is filtered off, washed with a mixture of methanol-water and dried in vacuo.

The yield of TLC-pure estradiol-17$\beta$, 3-N-bis(2-chloroethyl)carbamate(Estramastine) is 21.2 g (87.6%) which sinters at 65°–70° C. and melts at 124°–125° C.

Using the same molar ratios and reaction conditions, the above reaction is carried out with methylene chloride as solvent. The results are similar to those obtained with chloroform.

Changing the molar ratio estradiol:4-N,N-dimethylaminopyridine to 1:0.05 and increasing the reaction time to 6 hrs gives the same yield and quality of the end product as with the molar ratio mentioned above.

Using the same molar ratios but with a reaction temperature of 85° C. the above reaction is carried out with toluene as solvent. The results are similar to those obtained with chloroform and methylene chloride.

EXAMPLE 2

In order to study the selectivity of the reaction in Example 1, a reaction is carried out with excess N-bis(2-chloroethyl)carbamoyl chloride according to the following description.

To a stirred suspension of 15 g of estradiol-17$\beta$ (55 mmol), 12.54 g of triethylamine (124 mmol) and 3.0 g of 4-N,N-dimethylaminopyridine (24 mmol) in 200 ml of chloroform is added a solution of 26.4 g N-bis(2-chloroethyl)carbamoyl chloride (130 mmol) in 100 ml of chloroform. The mixture is vigorously stirred for 3 hrs at room temperature. A clear solution is obtained.

The solution is washed with 150 ml of 0.5-M hydrochloric acid and then twice with 150 ml portions of water. The organic phase is dried over sodium sulphate, filtered and evaporated to dryness.

The residual oil, which is the estradiol-17β, 3-N-bis(2-chloroethyl)carbamate, is recrystallized from 200 ml of methanol. The crystallized product is filtered off, washed with a mixture of methanol-water and dried in vacuo.

The yield of TLC-pure estradiol-17β, 3-N-bis(2-chloroethyl)carbamate is 22.5 g (92.8%) which sinters at 65°–70° C., solidifies and melts at 124°–125° C.

Using the same conditions as in the above example the 4-N,N-dimethylaminopyridine is replaced by 4-N,N-diethylaminopyridine and 4-(1-pyrrolidinyl)pyridine respectively. The results are similar to those obtained above.

Using the same molar ratios but with a reaction temperature of 85° C. the above reaction was carried out with toluene as solvent. The results are similar to those obtained with chloroform.

EXAMPLE 3

To a stirred suspension of 13.5 g of estradiol-17β (50 mmol), 5.55 g of triethylamine (55 mmol) and 1.5 g of 4-N,N-dimethylaminopyridine (12 mmol) in 150 ml of chloroform, is added a solution of 6.78 g diethylcarbamoyl chloride (50 mmol) in 50 ml of chloroform.

The mixture is vigorously stirred for 12 hrs at room temperature. Unreacted estradiol-17β is filtered off and the remaining clear solution is washed with 100 ml of 0.5-M hydrochloric acid and then twice with 100 ml portions of water. The organic phase is dried over sodium sulphate, filtered and evaporated to dryness.

The residual oil, which is the estradiol-17β, 3-N-diethylcarbamate, is recrystallized from 140 ml of methanol. The crystallized product is filtered off, washed with a mixture of methanol and water and dried in vacuo.

The yield of TLC-pure estradiol-17β, 3-N-diethylcarbamate is 6.0 g (32%) with a melting point 198°–200° C.

EXAMPLE 4

To a stirred suspension of 15 g of estradiol-17⊖ (55 mmol), 6.27 g of triethylamine (62 mmol) and 1.5 g of 4-N,N-dimethylaminopyridine (12 mmol) in 150 ml of chloroform, is added a solution of 19.06 g N-bis(2-bromoethyl)carbamoyl chloride (65 mmol) in 50 ml of chloroform.

The mixture is vigorously stirred for 3 hrs at room temperature. A clear solution is obtained. The solution is washed with 50 ml of 0.5-M hydrochloric acid and then twice with 100 ml portions of water. The organic phase is dried over sodium sulphate, filtered and evaporated to dryness.

The residual oil, which is the estradiol-17β, 3-N-bis(2-bromoethyl)carbamate, is recrystallized from 200 ml of methanol. The crystallized product is filtered off, washed with a mixture of methanol-water and dried in vacuo.

The yield of TLC-pure estradiol-17β, 3-N-bis(2-bromoethyl)carbamate is 24.7 g (85%) with a melting point of 80° C.

Using the same molar ratios and reaction conditions the above reaction is carried out with N-bis(2-chloropropyl)carbamoyl chloride.

The yield of TLC-pure estradiol-17β, 3-N-bis(2-chloropropyl)carbamate is 21.1 g (82%) with a melting point of 114°–116° C.

Using the same molar ratios and reaction conditions the above reaction is carried out with N-(2-chloroethyl)-N-(3-chloropropyl)carbamoyl chloride.

The yield of TLC-pure estradiol-17β, 3-N-(2-chloroethyl)-N-(3-chloropropyl)carbamate is 19.7 g (79%) with a melting point of 79°–87° C.

EXAMPLE 5

According to Example 1 and with chloroform as solvent, the 4-N,N-dimethylaminopyridine is replaced by the same molar amount of: 4-N,N-dimethylamino-3-methyl pyridine, 4-N,N-dimethylamino-3-ethyl pyridine, 4-N,N-diethylaminopyridine, 4-(1-pyrrolidinyl)-pyridine, 4-(1-piperidinyl)pyridine, 4-(4-methyl-1-piperidinyl)pyridine, 4-(1-hexahydroazepinyl)pyridine and 4-(1-morpholino)pyridine respectively.

The yields and purity of the estradiol-17β, 3-N(2-chloroethyl)carbamate obtained are similar to those obtained with 4-N,N-dimethylaminopyridine.

EXAMPLE 6

According to Example 1 and with chloroform as solvent, the estradiol-17β is replaced by the same molar amounts of: Estradiol-17α, Estriol, Estriol-16α-acetate, 16-ketoestradiol and 17α-ethinylestradiol respectively. The compounds obtained are pure according to TLC and their NMR-spectra are in accordance with the structures of the compounds named below. Yields and melting points of the pure compounds are shown.

Estradiol-17α, 3-N-bis(2-chloroethyl)carbamate (87%, m.p. 104.5°–106° C.)

Estriol-3-N-bis(2-chloroethyl)carbamate (80%, no defined melting point)

Estriol-16α -acetate-3-N-bis(2-chloroethyl)carbamate (75%, m.p. 154°–156° C.)

16-ketoestradiol-3-N-bis(2-chloroethyl)carbamate (70%, m.p. 199°–200° C.)

17α-ethynylestradiol-3-N-bis(2-chloroethyl)carbamate (72%, m.p. 140°–141° C.).

EXAMPLE 7

According to Example 1 and with chloroform as solvent, the triethylamine is replaced by: diisopropylethylamine and 1,8-bis(dimethyl-amino)naphtalene respectively.

The yields and purity of the estradiol-17 , 3-N(2-chloroethyl)carbamate obtained are similar to those obtained with triethylamine.

EXAMPLE 8

To illustrate the preparation of the active acylating complex 2.04 g (10 mmol) of N-bis(2-chloroethyl)carbamoyl chloride and 1.22 g (10 mmol) 4-N,N-dimethylaminopyridine are dissolved in 20 ml of deuterochloroform.

The solution obtained is analyzed by NMR.

The product formed (in solution) is 1-(N-bis(2-chloroethyl)aminocarbonyl)-4-dimethylaminopyridinium chloride, the structure of which is confirmed as stated by NMR.

The NMR data obtained are:

Chemical shift (peak structure, number of hydrogens);

Solvent: CDC13 3.45 (s, 6H), 3.9 (s, 8H), 7.35 (d, 2H), 8.65 (d, 2H).

EXAMPLE 9

To illustrate the isolation of the active acylation complex 8.16 g (40 mmol) of N-bis(2-chloroethyl)carbamoyl chloride and 4.88 g (40 mmol) of 4-N,N-dimethylaminopyridine are dissolved in 150 ml of chloroform.

The solution is allowed to stand for 24 hrs at room-temperature whereupon it is evaporated to dryness. The residual oil is treated with diethyl ether/acetone until crystallization takes place. The crystalline material is filtered off, washed with ether and dried in vacuo.

The product is 1-(N-bis(2-chloroethyl)aminocarbonyl)-4-dimethylaminopyridinium chloride. M.p. 162°–165° C. The structure is confirmed by NMR.

The NMR data obtained are:
Chemical shift (peak structure, number of hydrogens);
Solvent: CDCl3 3.45 (s, 6H), 3.9 (s, 8H), 7.35 (d, 2H), 8.65 (d, 2H).

Using the same conditions as in the above example the N-bis(2-chloroethyl)carbamoyl chloride is replaced by N,N-diethylcarbamoyl chloride. The isolated product is the 1-(N,N-diethylaminocarbonyl)-4-dimethylaminopyridiniumchloride. M.p. 95°–97° C.

The structure is confirmed by NMR.
The NMR data obtained are:
Chemical shift (peak structure, number of hydrogens);
Solvent: CDCl3 1.26 (t, 6H), 3.42 (s, 6H), 3.45 (q, 4H), 7.42 (d, 2H), 8.48 (d, 2H).

EXAMPLE 10

In order to study the rate of formation and the stability of the complexes formed, N-bis(2-chloroethyl)carbamoyl chloride and equimolar solutions in deuterochloroform of 4-N,N-di ethylaminopyridine and 4-pyrrolidinylpyridine respectively, are mixed and the NMR of the mixtures studied during a 24 hour period.

The study shows that the complexes are formed very rapidly and are stable in solution at room temperature.

The following NMR-data are obtained:
Chemical shift (peak structure number of hydrogens);
Solvent: CDCl3
1-(N-bis(2-chloroethyl)aminocarbonyl)-4-dimethylaminopyridinium chloride: 3.45 (s, 6H), 3.9 (s, 8H), 7.35 (d, 2H), 8.65 (d, 2H)
1-(N-bis(2-chloroethyl)aminocarbonyl)-4-diethylaminopyridinium chloride: 1.35 (t, 6H), 3.5–4.1 (m, 12H with a s, 8H at 3.9), 7.25 (d, 2H), 8.65 (d, 2H)
1-(N-bis(2-chloroethyl)aminocarbonyl)-4-(1-pyrrolidinyl)pyridinium chloride: 2.0–2.4 (m, 4H with a centrum at 2.2), 3.4–4.0 (m, 12H with a s, 8H at 3.9), 7.15 (d, 2H), 8.6 (d, 2H)

EXAMPLE 11

To illustrate performing the reaction in two steps with intermediary isolation of the acylating complex, the following experiments are performed: 8.08 g N-bis(2-chloroethyl)carbamoyl chloride (40 mmol) is dissolved in 150 ml of chloroform. To the solution is added 4.88 g of 4-N,N-dimethylaminopyridine (40 mmol) and the solution allowed to stand at room temperature for 24 hrs, whereupon it is evaporated to dryness.

The residual oil is treated with diethyl ether/acetone until crystallization takes place.

The crystalline material is filtered off, washed with ether and dried in vacuo.

6.23 g (20 mmol) of the isolated compound is dissolved in 100 ml of chloroform and 2.02 g of triethylamine (20 mmol) and 5.44 g of estradiol-17β are added. After vigorous stirring for 1 hour a clear solution is obtained, from which the estradiol-17β, 3-N-bis-(2-chloroethyl)carbamate could be isolated in the same manner as in Example 1.

Yield and purity are comparable to those obtained in Example 1.

The above reaction between the isolated complex and estradiol-17β is also carried out in the presence of only a minor amount (5 mmol) of triethylamine.

Yield and purity are comparable to those obtained in Example 1.

EXAMPLE 12

To a stirred solution of 23 ml of phosphorus oxychloride in 50 ml of dry pyridine is added a solution of 22 g (50 mmol) of estradiol-17β, 3-N-bis(2-chloroethyl)carbamate (prepared according to e.g. Example 1). The addition is carried out at a temperature of −10° C. The reaction mixture is allowed to stand at 0° C. for 1 hr, whereupon it is hydrolyzed by pouring it into a mixture of pyridine and ice-water. The solution is then added while stirring and cooling to a chilled mixture of hydrochloric acid and water. The precipitate thus obtained is filtered off, washed with water and dried in vacuo.

25 g of the dried product (which is the estradiol-17β, 3-N-bis(2-chloroethyl)carbamate-17-phosphate is dissolved while heating in a mixture of propan-2-ol, water and diluted hydrochloric acid. The solution is cooled to about 10° C. while agitating. The pure molecular complex between the estradiol-17β, 3-N-bis(2-chloroethyl)-carbamate-17-phosphate and propan-2-ol crystallizes from the solution. It is collected by filtration, washed with propan-2-ol and dried at 40° C. in vacuo.

20 g of the above propan-2-ol complex is dissolved in 200 ml of ethanol. This solution is slowly added to a solution of 4.95 g of sodium methylate dissolved in 150 ml of ethanol. The precipitated product is collected by filtration, washed with 200 ml of ethanol and dried at 35° C. in vacuo.

The compound obtained is the pure disodium salt of the estradiol-17β, 3-N-bis(2-chloroethyl)carbamate-17-phosphate, as a hydrate (as established by TLC, NMR, Karl Fisher titration, and elementary analysis).

We claim:
1. A selective acylation process for the preparation of phenolic N-disubstituted carbamate esters of steroids, comprising reacting in an inert solvent an acylating agent which is a carbamoyl halogenide plus a 4-(tertiary amino)-pyridine, or a complex of the two, and a steroid having a cyclopentanopolyhydrophenanthrene carbon-carbon skelton and having at least two free hydroxy groups attached to different carbon atoms of the carbon-carbon skeleton, at least one being phenolic and at least one being alcoholic, thereby to selectively acylate the phenolic hydroxy group.

2. A process according to claim 1, wherein the carbamoyl halogenide is a substituted N-dialkyl carbamoyl halide.

3. A process according to claim 2, wherein the alkyl groups are the same and different and are selected from ethyl or propyl, substituted with a halogen atom.

4. A process according to claim 3, wherein the carbamoyl chloride is N-bis(2-chloroethyl)carbamoyl chloride.

5. A process according to claim 1, wherein the phenolic steroid is an estra-1,3,5(10)-triene.

6. A process according to claim 5, wherein the estra-1,3,5(10)-triene is selected from estra-1,3,5(10)-triene-3,17β-diol (estradiol-17β), estra-1,3,5(10)-triene-3,17α-diol (estradiol-17α), estra-1,3,5,(10)-triene-3,16α,17β-triol (estriol), estra-1,3,5(10)-triene-3,16β,17β-triol (16-epiestriol), estra-1,3,5(10)-triene-3,16α,17α-triol (17-epiestriol), estra-1,3,5(10)-triene-3,16α-diol-17-one, estra-1,3,5(10)-triene-3,17β-diol-16-one (16-ketoestradiol), and 17α-ethynyl-estra-1,3,5(10)-triene-3,17β-diol (17α-ethynylestradiol), and monoesters of any foregoing triol at an alcoholic hydroxy group thereof.

7. A process according to claim 1, wherein the 4-(tertiary amino)pyridine is selected from 4-dimethylaminopyridine, 4-diethylaminopyridine, 4-pyrrolidinylpyridine, 4-piperidinylpyridine, 4-(4-methyl-1-piperidinyl)-pyridine, 4-morpholinylpyridine, and 4-hexahydroazepinylpyridine, preferably 4-dimethylaminopyridine and 4-pyrrolidinylpyridine.

8. A process according to claim 7, wherein the 4-tertiary amino)pyridine is employed in a catalytic amount, amd on the presence of an acid acceptor.

9. A process according to claim 8, wherein the catalytic amount of the 4-(tertiary amino)-pyridine is 0.02 to 0.2 mole per mole of the phenolic steroid.

10. A process according to claim 1, wherein the acid acceptor is a tertiary amine present in at least an amount necessary to bind free hydrogen halide formed during the reaction.

11. A process according to claim 1, wherein the complex is a 1-(N-disubstituted aminocarbonyl)-4-(tertiary amino)-pyridinium halogenide.

12. A process according to claim 10, wherein the complex is selected from 1-(N-bis(2-chloroethyl)aminocarbonyl)-4-dimethylaminopyridinium chloride and 1-(N-bis(2-chloroethyl)aminocarbonyl)-4-pyrrolidinylpyridinium chloride.

13. A process according to claim 1, wherein the solvent employed is selected from methylene chloride, chloroform, chlorobenzene, and toluene.

14. A process according to claim 1, wherein the carbamoyl halogenide is N-bis(2-chloroethyl)carbamoyl chloride and the starting steroid is estradiol-17β and the product is estradiol-3-N-bis(2-chloroethyl) carbamate.

15. A complex between N-disubstituted carbamoyl halogenide and 4-(tertiary amino)pyridine, which is 1-(N-disubstituted aminocarbonyl)-4-(tertiary amino)-pyridinium halogenide.

16. A complex according to claim 15, which is a 1-(N-bis(2-chloroethyl)aminocarbonyl)-4-(tertiary amino)-pyridinium chloride.

17. A complex according to claims 15 which is 1-(N-bis(2-chloroethyl)aminocarbonyl)-4-dimethylaminopyridinium chloride and 1-(N-bis(2-chloroethyl)aminocarbonyl)-4-pyrrolidinylpyridinium chloride.

18. A process according to claim 1, wherein the 4-(tertiary amino)-pyridine or a complex thereof with the carbamoyl halogenide is provided attached to or as a part of a polymer.

19. A process according to claim 1, wherein the reaction is carried out in the presence of an acid acceptor.

20. A process according to claim 3, wherein the alkyl group is substituted with a bromine or chlorine atom in the omega position.

21. A process according to claim 5, wherein the estra-1,3,5(10)-triene is estradiol-17 beta, estriol, estriol-16-acetate, or 17 alpha-ethynyl-estradiol.

22. A process according to claim 5, wherein the estra-1,3,5(10)-triene is estradiol-17 beta.

23. A process according to claim 1, wherein the 4-(tertiary amino)-pyridine is 4-dimethylaminopyridine or 4-pyrrolidinylpyridine.

* * * * *

UNITED STATES PATENT AND TRADEMARK OFFICE
CERTIFICATE OF CORRECTION

PATENT NO. : 4,592,869

DATED : June 3, 1986

INVENTOR(S) : Sten K. Kristensson and Anders R. Stamvik

It is certified that error appears in the above-identified patent and that said Letters Patent is hereby corrected as shown below:

Col. 2, line 8; "-(17-epiestriol)," should read -- -(17-epi-estriol), --
Col. 2, line 56; "-pyridinum" should read -- pyridinium --
Col. 2, line 59; after "(2-chloroethyl)" insert -- aminocarbonyl) --
Col. 4, line 40; "-(Estramastine)" should read -- -(Estramustine) --
Col. 5, line 43; "17θ" should read -- 17β --
Col. 7, line 37; "-di ethylaminopyridine" should read -- diethylaminopyridine --
Col. 7, line 43; after "structure" insert a comma -- , --
Col. 8, line 52; "carbamol" should read -- carbamoyl --

Col. 8, line 55; "skelton" should read -- skeleton --

Col. 8, line 64; "and" (first occurrence) should read -- or --
Col. 8, line 65; "or" should read -- and --
Col. 9, lines 20&21; put a period -- . -- after "hexahydroazepinylpyridine" and delete the rest of that claim.
Col. 9, line 24; "amd on" should read -- and in --
Col. 9, line 28; "claim 1" should read -- claim 19 --
Col. 10, line 17; "claims 15" should read -- claim 15, --

Signed and Sealed this

Ninth Day of December, 1986

*Attest:*

DONALD J. QUIGG

*Attesting Officer*   Commissioner of Patents and Trademarks